United States Patent
Röbelt et al.

(10) Patent No.: US 10,624,777 B2
(45) Date of Patent: Apr. 21, 2020

(54) VARIABLE BACK SHELL HAVING TWO SIDE SHELL PARTS

(71) Applicant: BAUERFEIND AG, Zeulenroda-Triebes (DE)

(72) Inventors: Gerhard Röbelt, Zeulenroda-Triebes (DE); Gerald Stier, Langenwetzendorf (DE); Ronny Baetz, Vogtländisches Oberland OT Pöllwitz (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 171 days.

(21) Appl. No.: 14/410,820

(22) PCT Filed: Jun. 28, 2013

(86) PCT No.: PCT/EP2013/063606
§ 371 (c)(1),
(2) Date: Dec. 23, 2014

(87) PCT Pub. No.: WO2014/001493
PCT Pub. Date: Jan. 3, 2014

(65) Prior Publication Data
US 2015/0182369 A1    Jul. 2, 2015

(30) Foreign Application Priority Data

Jun. 29, 2012 (DE) .......................... 10 2012 013 175

(51) Int. Cl.
*A61F 5/00* (2006.01)
*A61F 5/02* (2006.01)

(52) U.S. Cl.
CPC .................................. *A61F 5/022* (2013.01)

(58) Field of Classification Search
CPC .. A61F 5/02; A61F 5/022; A61F 5/024; A61F 5/026; A61F 5/028; A61F 5/03;
(Continued)

(56) References Cited

U.S. PATENT DOCUMENTS 2,269,681 A * 1/1942 Nathanson ............... A41C 1/08
128/96.1
4,202,327 A * 5/1980 Glancy ................... A61F 5/022
602/19
(Continued)

FOREIGN PATENT DOCUMENTS

DE         19855923 A1    6/2000
DE       202005011650 U1   11/2006
(Continued)

OTHER PUBLICATIONS

English Translation of International Preliminary Report on Patentability regarding International Application No. PCT/EP2013/063606.
(Continued)

*Primary Examiner* — Keri J Nelson
*Assistant Examiner* — Adam Baker
(74) *Attorney, Agent, or Firm* — Stephen T. Olson; Harness, Dickey & Pierce, P.L.C.

(57) ABSTRACT

The invention relates to a variable orthopaedic back shell having two side shell parts, which can be used as a back orthosis or as a holder for other orthoses, for example shoulder orthoses. The invention also relates to an orthosis which includes a back shell according to the invention, and to the orthopedic use of the back shells.

25 Claims, 5 Drawing Sheets

(58) Field of Classification Search
CPC .... A61F 5/055; A61F 5/04; A61F 5/05; A61F 5/058; A61F 5/0553; A41D 13/0525; A41D 13/0531; A41D 13/05
USPC ...... 602/16, 19, 5–7, 60–63; 128/96.1, 99.1, 128/100.1
See application file for complete search history.

(56) References Cited

U.S. PATENT DOCUMENTS

| | | | |
|---|---|---|---|
| 4,508,110 A | 4/1985 | Modglin | |
| 4,688,558 A * | 8/1987 | Hooper, Jr. | A61F 5/022 2/44 |
| 4,735,196 A | 4/1988 | Krag et al. | |
| 5,911,697 A * | 6/1999 | Biedermann | A61F 5/028 602/19 |
| 6,319,216 B1 * | 11/2001 | Coligado | A61F 5/028 602/19 |
| 6,503,215 B1 | 1/2003 | Reinhardt et al. | |
| 6,702,770 B2 * | 3/2004 | Bremer | A61F 5/055 602/19 |
| 2004/0147861 A1 * | 7/2004 | Kozersky | A61F 5/022 602/19 |
| 2004/0220503 A1 * | 11/2004 | Kozersky | A61F 5/022 602/19 |
| 2013/0303955 A1 * | 11/2013 | Beitl | A61F 5/024 602/19 |
| 2014/0371646 A1 * | 12/2014 | Kozersky | A61F 5/026 602/19 |

FOREIGN PATENT DOCUMENTS

| | | |
|---|---|---|
| DE | 102009056710 A1 | 5/2011 |
| FR | 2968540 A1 | 6/2012 |
| GB | 0330775 * | 6/1929 |
| WO | WO-97/03627 A1 | 2/1997 |

OTHER PUBLICATIONS

International Search Report for PCT/EP2013/063606, ISA/EP, dated Oct. 22, 2013.
International Preliminary Report on Patentability with annexes, and their translation, ISA/EP, Munich, dated Sep. 1, 2014.

* cited by examiner

VARIABLE BACK SHELL HAVING TWO SIDE SHELL PARTS

CROSS-REFERENCE TO RELATED APPLICATIONS

This application is a 371 U.S. National Stage of International Application No. PCT/EP2013/063606, filed Jun. 28, 2013, which claims the priority to German Patent Application No. 10 2012 013 175.5, filed Jun. 29, 2012. The disclosures of the above applications are incorporated herein by reference.

DESCRIPTION

Field

The invention relates to orthopedic back shells that can be used as back orthotics or as a holder for other orthotics, for example, shoulder orthotics. The invention also relates to an orthotic comprising a back shell according to the invention and the orthopedic use of the back shell.

Background

Orthotics are therapeutic aids for the stabilization or support of the movement function of body parts. When providing patients with functional orthotics, the emphasis is on restoring and maintaining the mobility of the musculo-skeletal system. Orthotics can secure function, mobilize, support, limit movement, and/or provide correction. Orthotics may be used directly after trauma or postoperatively or in a conservative fashion, i.e., for restoring, for maintaining, or for protecting joint function, for example, in the case of degenerative disorders. In order to achieve the stability required by each application, one or more stabilizing elements are provided in the orthotics. As a rule, the stabilizing elements are designed in the shape of a rod or shell. Stabilizing elements designed in a shell shape surround the body part or joint to be stabilized, for example, the torso in the region of the lumbar spine, around more than half of its circumference.

Back orthotics are known, for example, from the publications DE 19855923 A1 and DE 20 2005 011 650 U1. A one-piece orthopedic back shell is known from DE 10 2009 056 710 A1. WO 97/03627 A1 describes a back shell that is connected to an abdominal shell by belts.

The technical problem of the invention is primarily the provision of orthopedic back shells that are adaptable in a simple and precise fashion to the body structure and body circumference of the wearer, for example, the patient, in particular in the lumbar spine and pelvic region, while at the same time providing good wearer comfort. In addition, an orthopedic back shell should be provided that is able to cover a broad spectrum of body sizes while providing anatomically correct stability.

SUMMARY

This technical problem is completely solved by the provision of an orthopedic back shell, the back shell comprising at least one first flexible side shell part and one second flexible side shell part, with the first side shell part and the second side shell part being connected to one another via at least one connector element and with the first side shell part and the second side shell part being connectable to one another in a variable fashion via the at least one connector element.

In an expanded embodiment, the back shell may additionally comprise at least one middle shell part.

The technical problem is also completely solved by the provision of an orthopedic back shell, with the back shell comprising at least one first flexible side shell part, one second flexible side shell part, and one middle shell part, with the first side shell part and the second side shell part each being connected to the middle shell part via at least one connector element and with the first side shell part and the second side shell part being connectable in a variable fashion to the middle shell part via the at least one connector element.

In an alternative embodiment, the first side shell part and the second side shell part may be connected to the middle shell part via overlapping surface regions.

Thus, the present invention solves the technical problem mentioned above by providing an orthopedic back shell comprising a plurality of shell parts, for example, two or three shell parts, with adjacent or overlapping shell parts each being connected in a variable fashion via at least one connector element and being connectable to one another via the at least one connector element.

The shells may thus be positioned relative to one another in a variable fashion, such that the back shell is adaptable in a simple and precise fashion to the body circumference and body structure of the wearer, in particular in the lumbar spine and pelvic region, and then be fixed in the desired position relative to one another such that the back shell remains adapted to the body circumference and body structure.

Naturally, such fixing may be reversed as necessary, for example, if body circumference changes.

The first side shell part may be the left or right side shell part. The second side shell part is then the respective other side shell part, i.e., the right or left.

The optional middle shell part is preferably positioned centrally on the patient's back.

In a preferred embodiment, the first side shell part and the second side shell part have the same dimensions, such that the two side shell parts or the two side shell parts and the at least one middle shell part can combine to form an approximately axially symmetrical back shell.

In a preferred embodiment, the first side shell part and the second side shell part can each surround at least one part of a person's back and one side of said person's waist.

In a preferred embodiment, the first side shell part and the second side shell part are connected to one another via overlapping surface regions.

In a preferred embodiment, the shell parts, in particular the first side shell part and the second side shell part, are made from a flexible plastic material. A suitable plastic material is composed, for example, of at least one polyamide or contains polyamides. Persons skilled in the art are aware of other suitable materials, in particular plastic materials having a suitable flexibility, for example, casting resins.

In a preferred embodiment, the first side shell part and the second side shell part are produced by plastic injection molding. Suitable plastic injection molding techniques for the production of orthotic parts, including stabilizing elements for orthotics, are known from the prior art.

The middle shell part may also be made of a flexible plastic material. However, it may be made from another material as well. The middle shell part is preferably also flexible. However, it may also be rigid, for example, in the region of the spine.

In a preferred embodiment, the first side shell part and the second side shell part each have at least one hole for attaching the at least one connector part. In a preferred embodiment, the middle shell part comprises at least one hole for attaching the at least one connector system.

In a preferred embodiment, the first side shell part and the second side shell part comprise at least three holes for attaching the at least one connector system. In a preferred embodiment, the middle shell part comprises at least three holes, in particular at least six holes, for attaching the at least one connector system.

The holes may be either round holes or oblong holes. If round holes are used, variability of attachment can be achieved, in particular by the number of round holes. If oblong holes are used, variability of attachment can be achieved, in particular by the length, bend, and positioning of the oblong holes.

In a preferred embodiment, the first side shell part and the second side shell part comprise a plurality of holes, in particular round holes, for attaching the at least one connector system. In a preferred embodiment, the middle shell part comprises a plurality of holes, in particular round holes, for attaching the at least one connector system. The shells with a plurality of holes may, for example, be embodied as shell-shaped perforated plates.

The orthopedic back shell according to one of the previous claims, wherein the at least one connector element is embodied as a nut-and-bolt connection, as a quick-release mechanism, or as a rivet connection.

In a preferred embodiment, the at least one connector element is embodied as a clip connection or as a slidable snap-on connection.

In a preferred embodiment, the at least one connector element is embodied as a Velcro connection. A Velcro connection between two shells allows for extremely variable positioning and attachment of the two shells to one another.

The technical problem of the invention is also solved by the provision of an orthopedic back shell, with the back shell comprising a first side shell part and a second side shell part, with the first side shell part and/or the second side shell part comprising at least one oblong hole, and with the first side shell part and the second side shell part being connected to one another via at least one connector element, said connector element extending through the at least one oblong hole.

An orthopedic back shell is particularly preferred according to the invention in which the back shell comprises at least one first flexible side shell part and at least one second flexible side shell part, with the first side shell part and the second side shell part being connected to one another via at least two connector elements, and with the first side shell part and the second side shell part being attachable to one another via the at least two connector elements in a variable fashion, with the first side shell part as well as the second side shell part having at least two oblong holes disposed one above the other and the first side shell part and the second side shell part being connected via the at least two connector elements, with one of the two connector elements extending through an oblong hole of the first side shell part and one oblong hole of the second side shell part, and with the uppermost oblong hole of the first side shell part and the uppermost oblong hole of the second side shell part having a different angle, and with the lowermost oblong hole of the first side shell part and the lowermost oblong hole of the second side shell part having a different angle.

In a preferred embodiment, the first side shell part as well as the second side shell part comprise at least three oblong holes disposed one above the other.

In a preferred embodiment, the middle oblong hole of the first side shell part and the middle oblong hole (24) of the second side shell part have a different angle.

In a preferred embodiment, the uppermost oblong hole and the lowermost oblong hole of the first side shell part are disposed vertically or virtually vertically, with the uppermost oblong hole and the lowermost oblong hole of the second side shell part being disposed horizontally or virtually horizontally.

In a preferred embodiment, the middle oblong hole of the first side shell part and the middle oblong hole of the second side shell part are disposed obliquely.

In a preferred embodiment, the middle oblong hole of the first side shell part and the middle oblong hole of the second side shell part are disposed transverse to one another.

In a preferred embodiment, the uppermost oblong hole and the lowermost oblong hole of the first side shell part are disposed vertically or virtually vertically, with the uppermost oblong hole and the lowermost oblong hole of the second side shell part being disposed horizontally or virtually horizontally and with the middle oblong hole of the first side shell part and the middle oblong hole of the second side shell part being disposed obliquely.

In a preferred embodiment, the orthopedic back shell comprises a first flexible shell part and a second flexible shell part. In a preferred embodiment, the orthopedic back shell does not comprise a middle part. In a preferred embodiment, the first side shell part is connected to the second side shell part via overlapping surface regions.

In a preferred embodiment, the first side shell part or the second side shell part comprises one oblong hole, two oblong holes, or three oblong holes. In a preferred embodiment, the first side shell part and the second side shell part comprise one oblong hole, two oblong holes, or three oblong holes.

In a preferred embodiment, the first side shell part and/or the second side shell part comprises at least two oblong holes, with the first side shell part and the second side shell part being connected to one another via two connector elements, with one connector element extending through each oblong hole.

In a preferred embodiment, the first side shell part of the orthopedic back shell comprises at least three oblong holes.

In a preferred embodiment, the first side shell part of the orthopedic back shell as well as the second side part comprise at least three oblong holes.

In a preferred embodiment, the first side shell part of the orthopedic back shell as well as the second side shell part comprise at least three oblong holes and the first side shell part and the second side shell part are connected to one another via at least three connector elements, with each of the three connector elements extending through one oblong hole of the first side shell part and one oblong hole of the second side shell part.

The present invention also solves the technical problem of the invention by providing an orthopedic back shell according to the invention, with the first side shell part as well as the second side shell part comprising at least three oblong holes disposed one above the other, and with the first side shell part and the second side shell part being connected to one another via at least three connector elements, with each of the three connector elements extending through one oblong hole of the first side shell part and one oblong hole of the second side shell part.

It is preferable for the uppermost oblong hole of the first side shell part and the uppermost oblong hole of the second side shell part to have a different angle, with the middle oblong hole of the first side shell part and the middle oblong hole of the second side shell part having a different angle, and with the lowermost oblong hole of the first side shell part and the lowermost oblong hole of the second side shell part having a different angle.

In a preferred embodiment, the at least two oblong holes of the first side shell part and the at least two oblong holes of the second side shell part are respectively disposed one above the other.

In a preferred embodiment, the three oblong holes of the first side shell part and the three oblong holes of the second side shell part are respectively disposed one above the other.

In a preferred embodiment, the uppermost oblong hole of the first side shell part and the uppermost oblong hole of the second side shell part have a different angle, with the lowermost oblong hole of the first side shell part and the lowermost oblong hole of the second side shell part having a different angle.

In a preferred embodiment, the uppermost oblong hole of the first side shell part and the uppermost oblong hole of the second side shell part have a different angle, with the middle oblong hole of the first side shell part and the middle oblong hole of the second side shell part having a different angle, and with the lowermost oblong hole of the first side shell part and the lowermost oblong hole of the second side shell part having a different angle.

In a preferred embodiment, the uppermost oblong hole and the lowermost oblong hole of the first side shell part are disposed vertically or virtually vertically, with the uppermost oblong hole and the lowermost oblong hole of the second side shell part being disposed horizontally or virtually horizontally.

In a preferred embodiment, the first side shell part and the second side shell part each comprise two oblong holes, with the first side shell part and the second side shell part overlapping and being connected to one another via at least two connector elements, with each connector element extending through one oblong hole of the first side shell part and one oblong hole of the second side shell part. Preferably, the at least two oblong holes of the first side shell part and the at least two oblong holes of the second side shell part are respectively disposed one above the other. Preferably, the uppermost oblong hole of the first side shell part is disposed vertically or virtually vertically and the uppermost oblong hole of the second side shell part is disposed horizontally or virtually horizontally. In a preferred embodiment, the lowermost oblong hole of the first side shell part is disposed vertically or virtually vertically and the lowermost oblong hole of the second side shell part is disposed horizontally or virtually horizontally. Alternately, the lowermost oblong hole of the first side shell part may also be disposed horizontally or virtually horizontally and the lowermost oblong hole of the second side shell part may be disposed vertically or virtually vertically.

In a preferred embodiment, the uppermost oblong hole and the lowermost oblong hole of the first side shell part are disposed vertically or virtually vertically, with the uppermost oblong hole and the lowermost oblong hole of the second side shell part being disposed horizontally or virtually horizontally, and with the middle oblong hole of the first side shell part and the middle oblong hole of the second side shell part being disposed obliquely.

The technical problem of the invention is also solved in an alternate embodiment by the provision of an orthopedic back shell, with the back shell comprising a first side shell part, a second side shell part, and a middle shell part, with the first side shell part, the second side shell part, and/or the middle shell part comprising at least one oblong hole, and with the first side shell part and the second side shell part being connected to the middle shell part via at least one connector element, with the connector element extending through the at least one oblong hole.

In a preferred embodiment, the uppermost oblong hole and the lowermost oblong hole of the first side shell part and the second side shell part are disposed vertically or virtually vertically, the uppermost oblong hole and the lowermost oblong hole of the middle shell part are disposed horizontally or virtually horizontally, and the middle oblong hole of the first side shell part and the middle oblong hole of the second side shell part are disposed in an oblique fashion.

In a preferred embodiment, the first and the second side shell parts each comprise three oblong holes and the middle shell part comprises at least three oblong holes or at least six oblong holes.

In a preferred embodiment, the first side shell part as well as the second side shell part of the orthopedic back shell comprise at least three oblong holes and the first side shell part and the second side shell part are each connected to the middle shell part via at least three connector elements, with each of the three connector elements extending through an oblong hole of the first side shell part and/or the second side shell part and through a hole, in particular an oblong hole, of the middle shell part.

The present invention also solves the technical problem of the invention in an alternate embodiment by the provision of an orthopedic back shell according to the invention, with the back shell comprising at least one first flexible side shell part, at least one second flexible side shell part, and at least one middle shell part, with the first side shell part and the second side shell part each being connected to the middle shell part via at least two connector elements, and with the first side shell part and the second side shell part being attachable to the middle shell part in a variable fashion, with the first side shell part as well as the second side shell part comprising at least two oblong holes disposed one above the other, and with the middle shell part comprising four oblong holes, two of which are disposed one above the other and two of which are disposed one next to the other, with each of the at least two connector elements for each side extending through one oblong hole of the first side shell part or one oblong hole of the second side shell part and with each of the at least two connector elements extending through an oblong hole of the middle shell part, and with the uppermost oblong hole of the first side shell part and the uppermost oblong hole of the second side shell part each having a different angle than the corresponding oblong hole of the middle shell part connected thereto via a connector element, and with the lowermost oblong hole of the first side shell part and the lowermost oblong hole of the second side shell part each having a different angle than the corresponding oblong hole of the middle shell part connected thereto via a connector element.

The present invention also solves the technical problem of the invention in an alternate embodiment by the provision of an orthopedic back shell according to the invention, with the back shell comprising at least one first flexible side shell part, at least one second flexible side shell part, and at least one middle shell part, with the first side shell part and the second side shell part each being connected to the middle shell part via at least three connector elements, and with the first side shell part and the second side shell part being attachable in a variable fashion to the middle shell part via the at least three connector elements each, with the first side shell part as well as the second side shell part comprising at least three oblong holes disposed one above the other, and with the middle shell part comprising six oblong holes, which are disposed one above the other in sets of three, with the two sets of three being disposed next one another, with each of the at least three connector elements per side extending through an oblong hole of the first or second side shell part and with each of the at least three connector elements per side extending through an oblong hole of the middle shell part, and with the uppermost oblong hole of the first side shell part and the uppermost oblong hole of the second side shell part each having a different angle than the corresponding oblong hole of the middle shell part connected thereto via a connector element, and with the middle oblong hole of the first side shell part and the middle oblong hole of the second side shell part each having a different angle than the corresponding oblong hole of the middle shell part attached thereto via a connector element, and with the lowermost oblong hole of the first side shell part and the lowermost oblong hole of the second side shell part each having a different angle from the corresponding oblong hole of the middle shell part connected thereto via a connector element.

The present invention also solves the technical problem of the invention in an alternate embodiment by the provision of an orthopedic back shell according to the invention, with the first side shell part, the second side shell part, and the middle shell part comprising at least three oblong holes disposed one above the other, and with the first side shell part and the second side shell part each being connected to the middle shell part via at least three connector elements, with each of the three connector elements per side extending through an oblong hole of the first side shell part or an oblong hole of the second side shell part, and with each of the three connector elements per side extending through an oblong hole of the middle shell part.

It is preferable for the uppermost oblong hole of the side shell parts and the uppermost oblong hole of the middle shell part to have a different angle, with the middle oblong hole of the side shell parts and the middle oblong hole of the middle shell part having a different angle, and with the lowermost oblong hole of the side shell parts and the lowermost oblong hole of the middle shell part having a different angle.

In a preferred embodiment, the three oblong holes of the first side shell part and the three oblong holes of the second side shell part are respectively disposed one above the other.

In a preferred embodiment, the middle shell part comprises three oblong holes that are disposed one above the other. In an alternate embodiment, the middle shell part comprises six oblong holes, with three holes each disposed one above the other and the two sets of three disposed next to one another.

When oblong holes are used, they may be positioned differently on the shells, for example, vertically or virtually vertically, or horizontally or virtually horizontally, or obliquely. Thus, the individual oblong holes may be positioned differently.

In a preferred embodiment, the uppermost oblong hole and the lowermost oblong hole of the side shell parts are disposed vertically or virtually vertically, with the uppermost oblong hole and the lowermost oblong hole of the middle shell part being disposed horizontally or virtually horizontally, and with the middle oblong hole of the middle shell part being oriented obliquely.

In a preferred embodiment, oblong holes disposed horizontally or virtually horizontally are at least twice as long as oblong holes disposed vertically or virtually vertically.

In a preferred embodiment, oblong holes disposed obliquely are shorter than oblong holes disposed horizontally or virtually horizontally and longer than oblong holes disposed vertically or virtually vertically.

In a preferred embodiment, the middle oblong holes are disposed obliquely, in a straight line, and thus in the mirror image of one another relative to the vertical axis. Thus, the middle intersection of these holes and therefore also the associated connector element is always located centrally in the horizontal direction.

The position of the middle connector element thus corresponds advantageously to the position of the theoretical rotational axis. As the shell halves are displaced horizontally, the theoretical rotational axis merely shifts somewhat in the vertical direction. During the rotation of the shell halves, the position of the rotational axis does not change. The middle connector element is thus the only nearly stationary element of the entire shell and is therefore preferably suitable for attaching other orthotic elements, such as a brace, for example.

The oblong holes may be straight or curved. In a preferred embodiment, the oblong holes disposed horizontally or virtually horizontally are curved, in particular slightly curved. In a preferred embodiment, the oblong holes disposed vertically or virtually vertically and the oblong holes disposed obliquely are not curved.

In a preferred embodiment, the connector elements are embodied as nut-and-bolt connections, particularly when holes are used, preferably oblong holes. Other suitable connector elements, for example, quick-release mechanisms, are known to a person skilled in the art.

In a preferred embodiment, the back shell comprises an abdominal belt or a tension band system.

The present invention also relates to a back orthotic comprising an orthopedic back shell according to the invention.

The present invention also relates to the use of an orthopedic back shell according to the invention as a back orthotic.

The present invention also relates to the use of an orthopedic back shell according to the invention as a platform for a shoulder orthotic. Possible designs and constructions by means of which a shoulder orthotic may be attached to a back shell are known to a person skilled in the art.

BEST DESCRIPTION OF THE DRAWINGS

The figures described below illustrate an embodiment of the invention in the form of a variable back shell having two side shell parts. The teaching of the invention is not limited to this exemplary embodiment.

DETAILED DESCRIPTION

Example 1: Embodiment of a Back Shell According to the Invention Made of Two Side Shell Parts Each Having Three Oblong Holes FIGS. 1 to 5 show an orthopedic back shell (100) according to the invention having a first side shell part (1) and a second side shell part (2), with the first side shell part (1) having three oblong holes (13, 14, 15) disposed one above the other and with the second side shell part (2) having three oblong holes (23, 24, 25) disposed one above the other, and with the first side shell part (1) and the second side shell part (2) being connected to one another via three connector elements (31, 32, 33), with each of the three connector elements (33, 34, 35) extending through one oblong hole (13, 14, 15) of the first side shell part (1) and one oblong hole (23, 24, 25) of the second side shell part (2) and with the uppermost oblong hole (13) of the first side shell part (1) and the uppermost oblong hole (23) of the second side shell part (2) having a different angle, and with the middle oblong hole (14) of the first side shell part (1) and the middle oblong hole (24) of the second side shell part (2) having a different angle, and with the lowermost oblong hole (15) of the first side shell part (1) and the lowermost oblong hole (25) of the second side shell part (2) having a different angle.

The uppermost oblong hole (13) and the lowermost oblong hole (15) of the first side shell part (10) are disposed vertically or virtually vertically and the uppermost oblong hole (23) and the lowermost oblong hole (25) of the second side shell part (2) are disposed horizontally or virtually horizontally. The middle oblong hole (14) of the first side shell part (1) and the middle oblong hole (24) of the second side shell part (2) are disposed obliquely.

The uppermost oblong hole (23) and the lowermost oblong hole (25) of the second side shell part (2) are slightly curved.

The two shell halves (1, 2) may be moved translationally relative to one another in a horizontal fashion as well as rotated relative to one another. This rotation occurs around the human sagittal axis, by which only the axial direction from behind the body toward the front of the body is meant. The position of the axis is horizontally centered and conditionally movable in the vertical direction.

As a result, the two shell halves (1, 2) have a common theoretical rotational axis that maintains its central horizontal position even when both halves are moved horizontally.

The connection and guidance of the two parts (1, 2) is achieved by the oblong holes (13, 14, 15, 23, 24, 25) that are introduced, into which connector elements (33, 34, 35) extend, which allow only predetermined paths for the relative movement of the two parts (1, 2) relative to one another (similar to a cam mechanism).

The oblong holes (13, 14, 15, 23, 24, 25) are disposed in such a way that the holes on one shell half (1) always intersect with those of the second shell half (2) in order to guarantee a defined position of the connector element (33, 34, 35) extending through the holes by means of the resulting intersection.

Here, each half (1, 2) comprises three oblong holes (13, 14, 15, 23, 24, 25), one each above, below, and in the middle, although the pure guidance function could theoretically also be fulfilled without the uppermost oblong hole (13, 23). However, this could have an unfavorable effect on the overall stability of the shell. The outermost oblong holes (13, 23) of the left half (1) are vertical, while the outermost oblong holes (23, 25) of the right half (2) tend to have a horizontal orientation because they are not precisely horizontal, but rather have a slightly curved shape.

The large radius of this curve results from a compromise between the distance from the theoretical rotational axis and the curve desired by the structure, the shape of which is based on the shape of the shell edge.

The balance of this compromise is achieved in that the vertical oblong holes (13, 15) of the left shell half (1) are not designed as points (i.e., as holes), but rather are extended in the vertical direction and therefore regionally overlap the horizontal oblong holes (23, 25). As a result, the limit of the relative movement of the two halves (1, 2) is formed by the respective ends of the vertical oblong holes (13, 15) as well as by the ends of the horizontal holes (23, 25).

The middle oblong holes (14, 24) of both shell halves (1, 2) also overlap in one single intersection point. In this case, both oblong holes (14, 24) are oriented with a horizontal tendency, albeit somewhat diagonally, in a straight line, and thus in the mirror image of one another relative to the vertical axis. Thus, the central intersection point, and therefore also the associated connector element (34), is always located in the horizontal middle.

The position of the middle connector element (34) thus corresponds to the position of the theoretical rotational axis. As the shell halves (1, 2) are displaced horizontally, the theoretical rotational axis merely wanders somewhat in the vertical direction, specifically, as a function of the length of the vertical extension or the V angle of the diagonal middle oblong holes (14, 24). During the rotation of the shell halves (1, 2), the position of the rotational axis does not change.

The middle connector element (34) is therefore the only almost stationary element of the entire shell (100) and is therefore potentially most suitable for the attachment of other orthotic elements such as, for example, a brace.

Particularly because of the function of pushing the halves together and improved interlocking by the side shells (1, 2) in the horizontal direction as well as due to the round, torso-like shape, a very flexible shell material should be selected that also has sufficient ductility to guarantee the originally intended support function of the back shell (100).

The overlapping of the two shell halves (1, 2) is advantageously achieved by a mutual give between the two halves.

Connector elements (33, 34, 35) embodied as a locking mechanism allow the correct adjustment to be locked into place and the back shell (100) to be prepared for use.

An additional advantage of the above arrangement lies in the ability of the back shell (100) to better adapt itself to any scoliotic pelvis issues that may be present such that no unnecessary pressure points result when the patient is wearing the orthotic. The adjustment potential to that effect is the result of the adjustability of both shell halves (1, 2) relative to one another in a purely vertical direction. By combining the latter function with the rotation shown above, the extent of this form of adjustment is further expanded, as may be seen from FIGS. 4 and 5.

Figure 1:
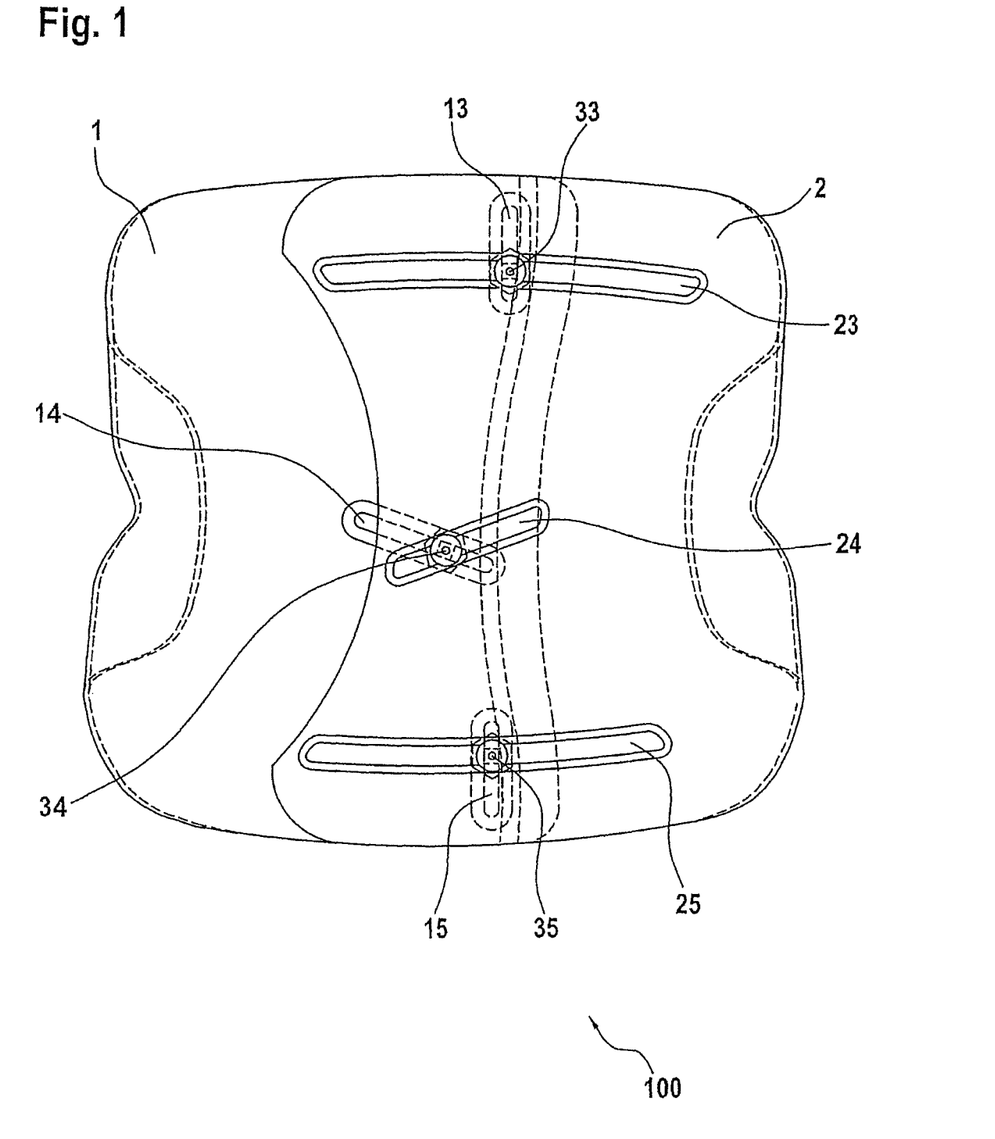
FIG. 1 shows an exemplary embodiment of a back shell according to the invention in a central position.
Figure 2:
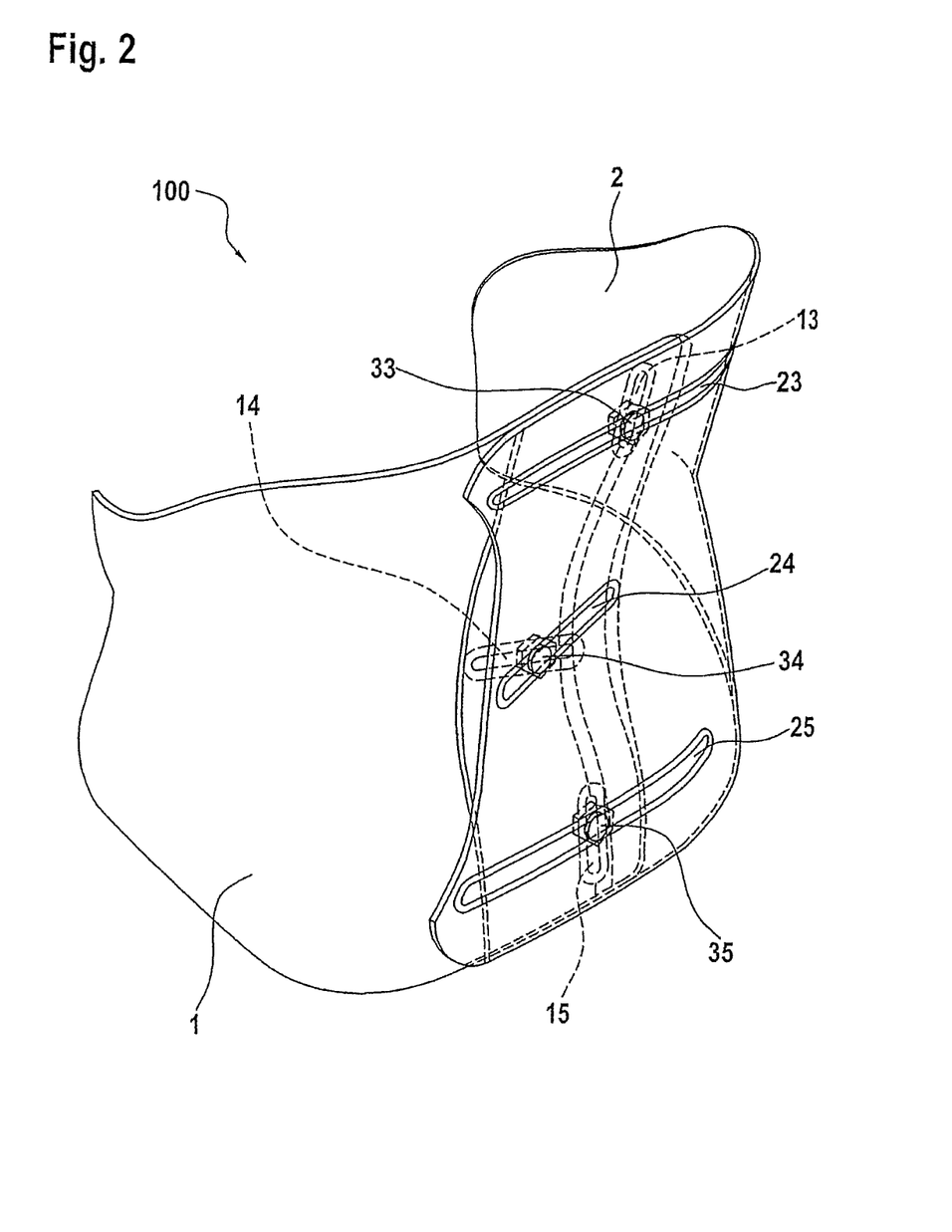
FIG. 2 shows a side view of the back shell according to the invention shown in a central position according to FIG. 1.
Figure 3:
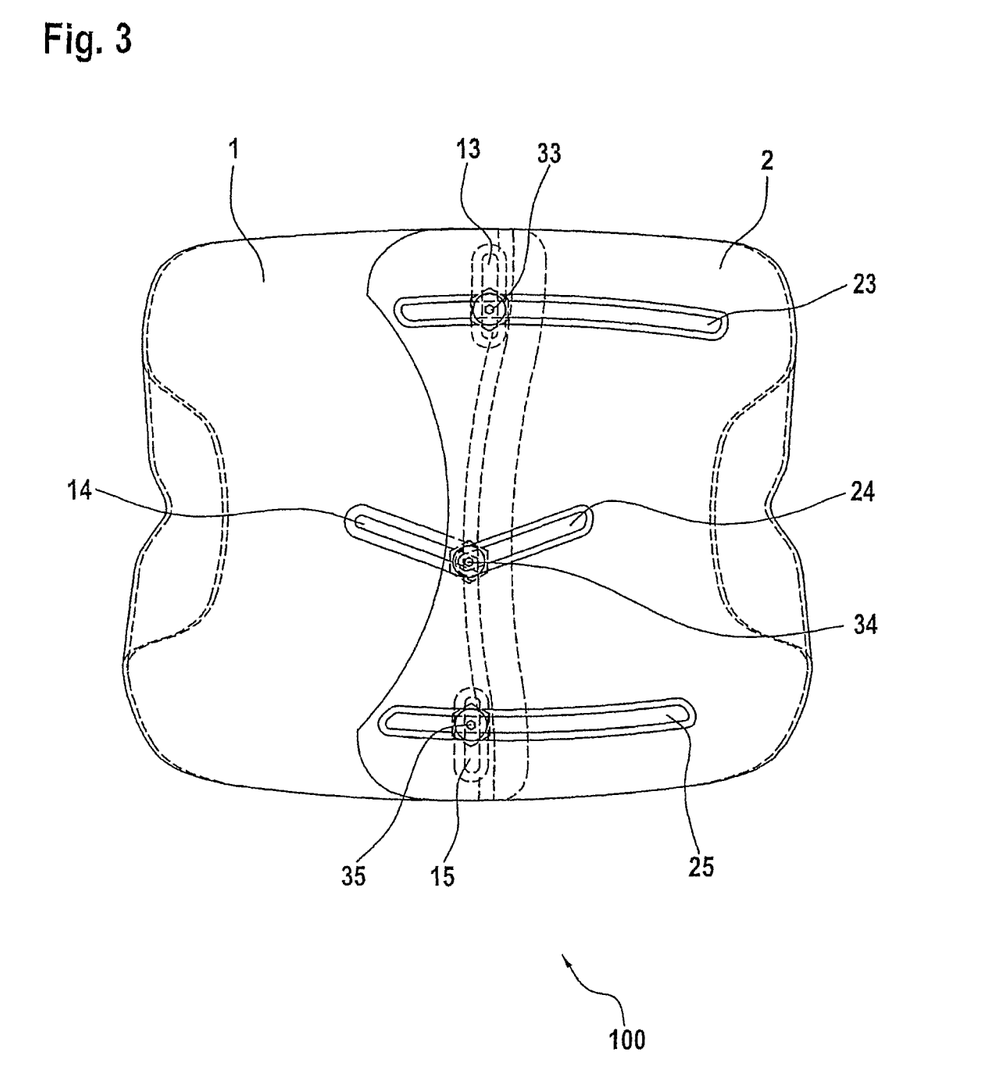
FIG. 3 shows the back shell according to the invention from FIG. 1 in the maximum position.

FIG. 1 shows the back shell (100) in a middle setting. FIG. 2 shows the side view of the back shell (100) in the middle setting. FIG. 3 shows the back shell (100) from FIG. 1 in the maximum setting.

Figure 4:
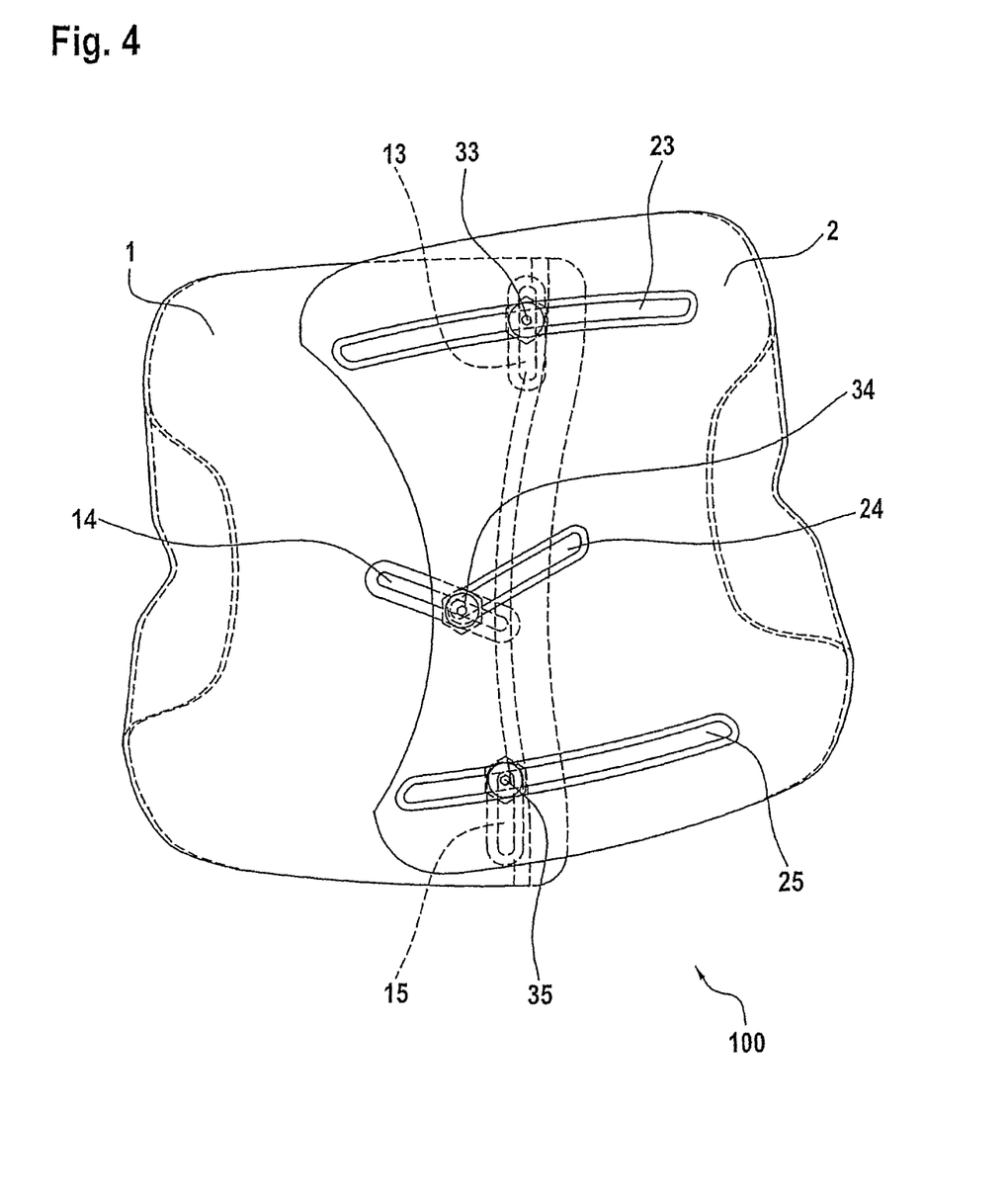
FIG. 4 shows the back shell according to the invention from FIG. 1 in the maximum position in the case of a scoliotic pelvis.
Figure 5:
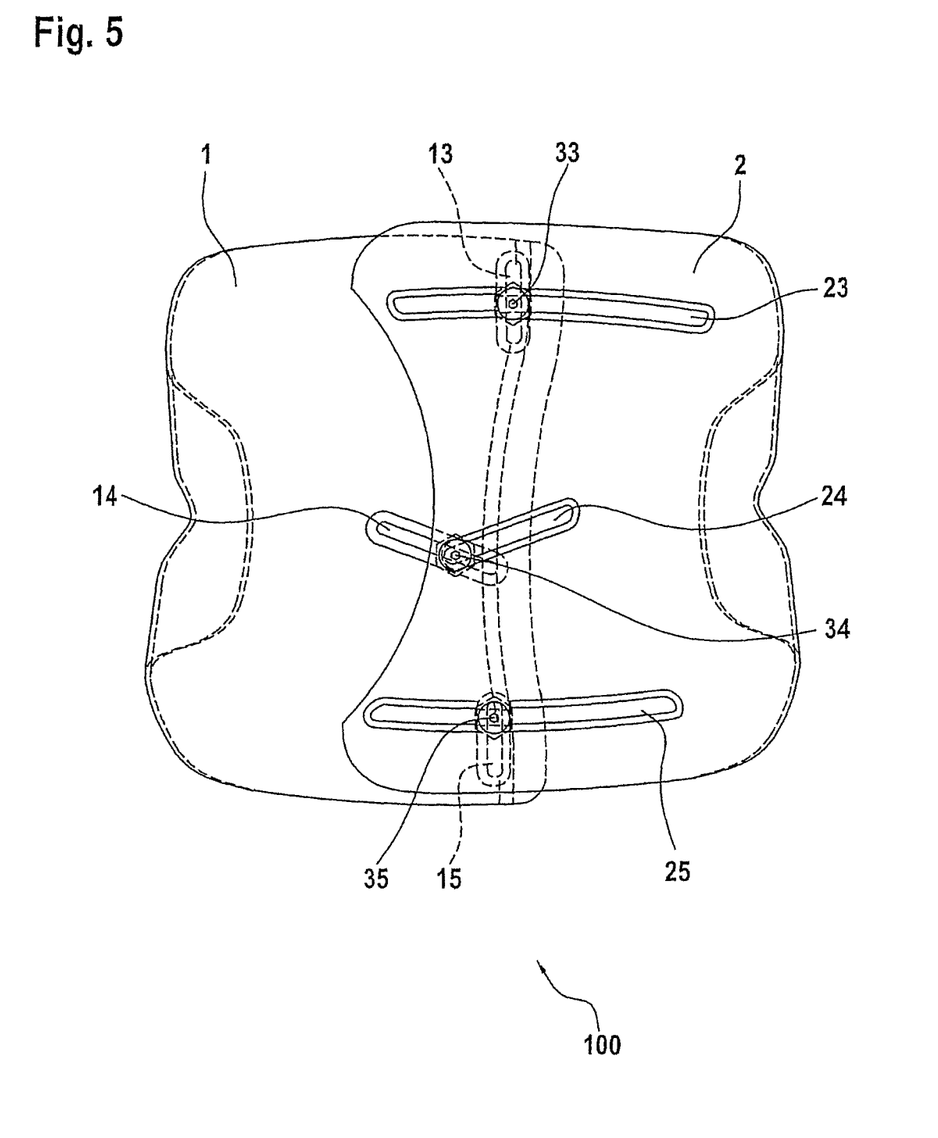
FIG. 5 shows the back shell according to the invention from FIG. 1 in the minimum position in the case of a scoliotic pelvis.

FIG. 4 shows the back shell (100) in the maximum setting in the case of a scoliotic pelvis, and FIG. 5 shows the back shell (100) in the minimum setting in the case of a scoliotic pelvis.

Example 2: Position and Length of the Oblong Holes

Advantageous positioning and length of the oblong holes on the two shell halves and a targeted arrangement of the same for the purpose of adjustability or adaptability of the horizontal dimension of the construct as well as the angle between the two shell halves upon rotation around the human sagittal axis can be easily determined by a mathematical model. In so doing, a position of the oblong holes can be found that provides a system for the connection and targeted guidance of the two shell halves that, in addition to the guidance characteristics, also offers a level of flexibility that has not been attained up to now.

The deciding feature in that regard is the presence of oblong holes with different orientations in each of the two shell parts that slide or are twisted relative to one another during adjustment and through which a specially constructed connector part is inserted that holds the two shell halves together. To this end, it is advantageous for the two halves to overlap one another at all times at least far enough that a connection of the two halves through the slots is even possible. Because two corresponding oblong holes always have a different orientation in their longitudinal direction, a fixed position of the correspondingly inserted convector part results.

Moreover, there is a systematic relationship between the horizontal and vertical position and the length of the oblong holes. However, the exact orientation of the latter is again a compromise between a mathematical system and technically favorable design parameters in this regard as well.

The precise position and length of the oblong holes can be easily calculated by a person skilled in the art using a suitable mathematical model.

An advantageous model assumes horizontal oblong holes that are straight rather than curved in order to approximate the core problem. The influence of horizontal expansion is more dominant in the system overall than the rotation because the latter occurs only in the angle range of −30° to +30°. In contrast, depending on the type of shell, horizontal adjustment may occur in the range of −40/80 mm to +40/80 mm. In practice, however, the design of the horizontal oblong holes as slight curves somewhat accommodates the rotational movement. The remaining positional differences that still result are absorbed by the longitudinal extension of the vertical oblong holes.

The invention claimed is:

1. An orthopedic back shell comprising:
a plurality of flexible side shell parts including a first flexible side shell part and a second flexible side shell part;
the first flexible side shell part and the second flexible side shell part connected to one another via overlapping surface regions,
the first flexible side shell part and the second flexible side shell part variably connected to one another via at least two connector elements, with the first flexible side shell part including at least two oblong holes disposed one above the other, the second flexible side shell part including at least two oblong holes disposed one above the other, the first flexible side shell part and the second flexible side shell part directly connected to one another via the at least two connector elements and with each of the two connector elements extending through one oblong hole of the first flexible side shell part and one oblong hole of the second flexible side shell part,
wherein an uppermost oblong hole and a lowermost oblong hole of the first flexible side shell part both extend virtually along a vertically extending line and an uppermost oblong hole and a lowermost oblong hole of the second flexible side shell part both extend virtually perpendicular to the uppermost and lowermost oblong holes of the first flexible side shell part,
wherein a center oblong hole of the first flexible side shell part and a middle oblong hole of the second flexible side shell part both extend obliquely relative to the vertically extending line and the center oblong hole of the first flexible side shell part and the middle oblong hole of the second flexible side shell part both intersect the vertically extending line.

2. The orthopedic back shell according to claim 1, wherein the first flexible side shell part is convexly curved in a horizontal direction and includes at least three oblong holes spaced apart from one another in a vertical direction and the second flexible side shell part includes at least three oblong holes spaced apart from one another in the vertical direction.

3. The orthopedic back shell according to claim 1, wherein the first flexible side shell part and the second flexible side shell part each are convexly curved in a horizontal direction to both surround at least part of the back and a side of the torso.

4. The orthopedic back shell according to claim 1, wherein the first flexible side shell part and the second flexible side shell part are made of a flexible plastic material.

5. The orthopedic back shell according to claim 1, wherein at least a first connector element of the at least two connector elements is selected from a group consisting of a nut-and-bolt connection, a quick-release mechanism, and a rivet connection.

6. The orthopedic back shell according to claim 1, wherein at least a first connector element of the at least two connector elements is selected from a group consisting of a clip connection, a Velcro connection, and a slidable locking connection.

7. The orthopedic back shell according to claim 1, wherein the back shell has an abdominal belt or a tension band system.

8. An orthopedic back shell according to claim 1, in combination with a back orthotic.

9. A method of using an orthopedic back shell according to claim 1 as a back orthotic, the method comprising:
surrounding at least a first part of the back and a first side of the torso with the first flexible side shell part;
surrounding at least a second part of the back and a second flexible side of the torso with the second side shell part.

10. A method of using an orthopedic back shell according to claim 1 as a platform for a shoulder orthotic.

11. The orthopedic back shell according to claim 1, wherein the uppermost and lowermost oblong holes on the first flexible side shell part are linear holes.

12. The orthopedic back shell according to claim 1, wherein the first and second flexible side shell parts are both curved to include a back portion and a side portion.

13. The orthopedic back shell according to claim 1, wherein the middle oblong hole and the center oblong hole are mirror images of one another relative to the vertically extending line.

14. The orthopedic back shell according to claim 1, wherein the orthopedic back shell includes a plurality of panels consisting of the first and second flexible side shell parts.

15. The orthopedic back shell according to claim 1, wherein the uppermost and lowermost oblong holes of the first flexible side shell part are spaced apart from one another in a vertical direction.

16. The orthopedic back shell according to claim 15, wherein the uppermost and lowermost oblong holes of the first flexible side shell part are elongated in a horizontal direction and an uppermost and a lowermost oblong hole of the second flexible side shell part are elongated in the vertical direction.

17. The orthopedic back shell according to claim 15, wherein the uppermost and lowermost oblong holes of the first flexible side shell part are curved.

18. The orthopedic back shell according to claim 1, wherein the orthopedic back shell includes a plurality of oblong holes including the uppermost oblong hole and the lowermost oblong hole of the first flexible side shell part, the uppermost oblong hole and the lowermost oblong hole of the first flexible side shell part, the center oblong hole of the first flexible side shell part, and the middle oblong hole of the second flexible side shell part, the plurality of oblong holes consisting of six oblong holes.

19. The orthopedic back shell according to claim 1, wherein the first and second flexible side shell parts are translationally movable relative to one another in a horizontal direction and rotationally movable relative to one another.

20. The orthopedic back shell according to claim 1, wherein the first and second flexible side shell parts have a common theoretical rotational axis that maintains a central horizontal position during relative horizontal movement between the first and second flexible side shell parts.

21. The orthopedic back shell according to claim 1, wherein the uppermost oblong hole and a lowermost oblong hole of the second flexible side shell are substantially longer than the uppermost oblong hole and a lowermost oblong hole of the first flexible side shell part.

22. The orthopedic back shell according to claim 1, wherein the center oblong hole of the first flexible side shell part and the middle oblong hole of the second flexible side shell part overlap at an intersection point, the intersection point located at a horizontal middle of the orthopedic back shell.

23. The orthopedic back shell according to claim 22, wherein the intersection point defines a theoretical rotational axis of the orthopedic back shell, the theoretical rotational axis limited to movement in a vertical direction during relative motion of the first and second flexible side shell parts about the theoretical rotational axis.

24. The orthopedic back shell according to claim 1, wherein the plurality of flexible side shell parts consists of the first and second flexible side shell parts.

25. An orthopedic back shell comprising:
a plurality of flexible side shell parts including a first flexible side shell part and a second flexible side shell part;
the first flexible side shell part and the second flexible side shell part connected to one another via overlapping surface regions,
the first flexible side shell part and the second flexible side shell part variably connected to one another via at least two connector elements, with the first flexible side shell part including at least two oblong holes disposed one above the other, the second flexible side shell part including at least two oblong holes disposed one above the other, the first flexible side shell part and the second flexible side shell part directly connected to one another via the at least two connector elements and with each of the two connector elements extending through one oblong hole of the first flexible side shell part and one oblong hole of the second flexible side shell part,
wherein an uppermost oblong hole and a lowermost oblong hole of the first flexible side shell part both extend virtually along a vertically extending line and an uppermost oblong hole and a lowermost oblong hole of the second flexible side shell part both extend virtually perpendicular to the uppermost and lowermost oblong holes of the first flexible side shell part, wherein a center oblong hole of the first flexible side shell part and a middle oblong hole of the second flexible side shell part both extend obliquely relative to the vertically extending line and the center oblong hole of the first flexible side shell part and the middle oblong hole of the second flexible side shell part both intersect the vertically extending line, and wherein the uppermost oblong hole and a lowermost oblong hole of the second flexible side shell are substantially longer than the uppermost oblong hole and a lowermost oblong hole of the first flexible side shell part.

* * * * *